United States Patent
Jacobs et al.

(10) Patent No.: US 7,141,555 B2
(45) Date of Patent: Nov. 28, 2006

(54) MODAFINIL COMPOUND AND CYCLODEXTRIN MIXTURES

(75) Inventors: Martin J. Jacobs, West Chester, PA (US); Piyush R. Patel, Wallingford, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 10/023,441

(22) Filed: Dec. 18, 2001

(65) Prior Publication Data

US 2002/0160982 A1 Oct. 31, 2002

Related U.S. Application Data

(60) Provisional application No. 60/256,681, filed on Dec. 19, 2000.

(51) Int. Cl.
*A61K 31/724* (2006.01)
*A61K 31/165* (2006.01)

(52) U.S. Cl. .......................... 514/58; 514/618
(58) Field of Classification Search ............... 514/103, 514/618, 58
See application file for complete search history.

(56) References Cited

U.S. PATENT DOCUMENTS

| | | | |
|---|---|---|---|
| 4,177,290 A | 12/1979 | Lafon | 424/324 |
| 4,565,807 A | 1/1986 | Uekama et al. | 514/58 |
| 4,727,064 A | 2/1988 | Pitha | 514/58 |
| 4,927,855 A | 5/1990 | Lafon | 514/618 |
| 5,024,997 A | 6/1991 | Motola et al. | 514/58 |
| 5,180,745 A | 1/1993 | Lafon | 514/618 |
| 5,391,576 A * | 2/1995 | Lafon | 514/618 |
| 5,618,845 A | 4/1997 | Grebow et al. | 514/618 |
| 5,843,347 A | 12/1998 | Nguyen et al. | 264/9 |
| 5,866,162 A | 2/1999 | Grattan | 424/466 |
| 6,077,871 A | 6/2000 | Campeta | 514/648 |
| 6,200,968 B1 | 3/2001 | Dickason et al. | 514/211.09 |
| RE37,516 E | 1/2002 | Grebow et al. | 514/618 |
| 6,346,548 B1 * | 2/2002 | Miller et al. | 514/618 |
| 6,455,588 B1 * | 9/2002 | Scammell et al. | 514/618 |

FOREIGN PATENT DOCUMENTS

FR 2 702 968 9/1994
WO WO 94/21371 9/1994

OTHER PUBLICATIONS

Pitha, J. et al "Hydroxypropyl-b-cyclodextrin: preparation and characterization" Int. J. Pharm. (1986) vol. 29, pp. 73-82.*
Hedges, A. "Industrial applicationf of Cyclodextrins" Chem. Rev. (1998) vol. 98, pp. 2035-2044.*
Loftsson, T. et al "Pharmaceutical applications of cyclodextrins" J. Pharm. Sci. (1996) vol. 85, No. 10, pp. 1017-1025.*
Spirichev, V. B. et al "Study of bioavailability of different forms of synthetic beta-carotene in volunteers" Vopr. Pitan. (1996) vol. 6, pp. 22-26 (abstract only).*
Westerberg, G. et al "Beta-cyclodextrin reduces bioavailability of orally administered [3H]benzo[a]pyrene in the rat" J. Pharm. Sci. (2005).*
Hostetler, J. et al "Effect of cyclodextrin on the pharmacology . . . " Antimicrob. Agents Chemother. (1992) vol. 36, No. 2, pp. 477-480.*
Nakanishi, K. et al "Effect of teh interaction of drug-beta-cyclodextrin complex with bile salts . . . " Chem. Pharm. Bull. (1989) vol. 37, No. 1, pp. 211-214.*
Szejtli, J. "Introduction and general overview of cyclodextrin chemistry" Chem. Rev. (1998) vol. 98, pp. 1743-1753.*
CyDex presentation on Captisol® (http://www.cydexinc.com/maxdocs/Cyclodextrin-derivatives.pdf, accessed Apr. 6, 2006).*
Rambert, F.A. et al., *Neuropschychopharmacology*, 1994, 10(3S), 169S.
Uekama, K. et al., *CRC Critical Reviews in Therapeutic Drug Carrier Systems*, 1987, 3(1), 1-40.
Parrish, M.A., *Cyclodextrins*.
Loftsson, T., *Pharmaceutical Technology*, 1999, 12, 40-50.
Duchêne, D. et al., *Drug Dev. Ind. Pharm.*, 1986, 12(11-13), 2193-2215.
Szente, L. et al., *Journal of Inclusion Phenomena*, 1984, 2, 631-636.
Pagington, J.S., *Chemistry in Britain*, 1987, 455-458.
Wen-lu, S. et al., *Chemosphere*, 1999, 38(4), 693-698.
Ammar, H. O. et al., *Pharmazie*, 1995, 50, 805-808.
Masson et al., *Journal of Controlled Release*, 1999, 59, 107-118.
Nakanishi, K. et al., *Chem. Pharm. Bull.*, 1992, 40, 1252-1256.
Challa et al., *AAPS PharmSciTech*, 2005, 6, E329-E357.

* cited by examiner

*Primary Examiner*—Leigh C. Maier
(74) *Attorney, Agent, or Firm*—Cephalon, Inc.

(57) ABSTRACT

Mixtures of a modafinil compound with a cyclodextrin, methods for their use, and compositions thereof are disclosed, along with complexes comprising a modafinil compound and a cyclodextrin which are taste-masked and suitable for oral consumption in an aqueous solution.

36 Claims, 1 Drawing Sheet

MODAFINIL COMPOUND AND CYCLODEXTRIN MIXTURES

This Application: claims benefit of U.S. Provisional Application Ser. No. 60/256,681 filed Dec. 19, 2000.

FIELD OF THE INVENTION

This invention relates to complexes of a modafinil compound with a cyclodextrin, a method for their use, and compositions thereof. In particular, the invention relates to complexes comprising a modafinil compound and a cyclodextrin in an aqueous solution that is suitable for oral administration.

BACKGROUND OF THE INVENTION

Modafinil ($C_{15}H_{15}NO_2S$), is 2-(benzhydryl-sulfinyl)acetamide, and is also known as 2-[(diphenylmethyl) sulfinyl] acetamide.

Modafinil has been described as presenting a "neuropsychopharmacological spectrum characterized by the presence of excitation with hyperactivity and of hypermotility; and by the absence of stereotypy (except in high doses) and of potentialization of the effects of apomorphine and amphetamine" (U.S. Pat. No. 4,177,290; hereinafter the "'290 patent," which is incorporated in its entirety herein by reference). A single administration of modafinil results in increased locomotor activity in mice and increased nocturnal activity in monkeys. Duteil et al., *Eur. J. Pharmacol.,* 1990, 180, 49. Modafinil has been successfully tested in humans for treatment of idiopathic hypersomnia and narcolepsy. Bastuji et al., *Prog. Neuro-Psych. Biol. Psych.,* 1988, 12, 695.

Other uses of modafinil have been presented. U.S. Pat. No. 5,180,745, incorporated in its entirety herein by reference, discloses the use of modafinil for providing a neuroprotective effect in humans, and in particular for the treatment of Parkinson's disease. The levorotatory form of modafinil, i.e.,(−)benzhydrylsulfinyl-acetamide, may have potential benefit for treatment of depression, hypersomnia and Alzheimer's disease (U.S. Pat. No. 4,927,855, incorporated in its entirety herein by reference). European Published Application 547952 (published Jun. 23, 1993) discloses the use of modafinil as an anti-ischemic agent. European Published Application 594507 (published Apr. 27, 1994) discloses the use of modafinil to treat urinary incontinence.

Preparations of modafinil having a defined solid particle size have been described in U.S. Pat. No. 5,618,845, incorporated in its entirety herein by reference, and preparations of a levorotatory isomer of modafinil was described in U.S. Pat. No. 4,927,855. Heterocyclic derivatives of modafinil are disclosed in U.S. patent 5 application Ser. No. 60/204,789, incorporated in its entirety herein by reference.

Modafinil has been approved for use in humans in 100 mg and 200 mg solid unit dose forms in the U.S. It is also desirable to formulate modafinil in liquid compositions. However, formulation of modafinil in liquid compositions is hampered by the low solubility and unpleasant taste of the modafinil compound. It is desirable to formulate compositions that effectively taste-mask the modafinil compound and provide a therapeutically effective amount of the same. It has been found that use of a complexing agent can achieve these goals, thereby enhancing the pharmacological properties of compositions of modafinil compound. The use of cyclodextrins allow for the formulation of a modafinil compound in aqueous solutions suitable for oral administration, and provide for more efficient absorption of the drug by the body.

Cyclodextrins ("CD's") are well-known and are the subject of many reviews.

See for example, J. Szejtli, *Cyclodextrins and their Inclusion Complexes* Budapest:Akademiai Kiado (1982); Loftsson, T., *Pharm. Technol. Eur.* 1999, 11(10), 2032 and J. S. Pagington, *Chemistry in Britain,* 1987, 5, 455–458. They consist of glucose units linked in a ring configuration, and more specifically, they are cyclic oligosaccharides composed of α-(1,4)-linked D-glucopyranosyl units. The cyclodextrin molecules have essentially a toroidal or donut shape, with an interior lipophilic cavity and a hydrophobic exterior. The most common cyclodextrins are the naturally occurring α-, β-, and γ-forms, which consist of 6, 7 and 8 glucopyranose units respectively, with the respective cavities having a diameter of 5.7 Å, 7.8 Å, and 9.5 Å. Inclusion complexes are formed when a guest molecule fits partially or entirely within the lipophilic cavity of the cyclodextrin. The driving force for complex formation is the displacement of water molecules by the more hydrophobic guest molecule. The degree and stability of complexation depends on how well the guest molecule, or portions of it, fit within the cavity of the cyclodextrin. The exterior of the cyclodextrin molecule is hydrophilic, which can enhance the aqueous solubility of the complex, and thereby the solubility of the guest molecule.

Cyclodextrin compositions have found some application in the pharmaceutical industry. See Uekama, K, et al., *CRC Critical Reviews in therapeutic Drug Carrier Systems,* 1987, 3(1), 1–40; Duchene, D, et al., *Drug Dev. Ind. Pharm.,* 1986, 12(11–13) 2193–2215. For example, compositions of Droloxifene in various cyclodextrins are described in U.S. Pat. No. 6,077,871. Solubilization of ibuprofen in cyclodextrin solutions have been described in various patents, including U.S. Pat. No. 5,024,997, U.S. Pat. No. 4,727,064 and U.S. Pat. No. 5,866,162. Pirprofen and cyclodextrin compositions were disclosed in U.S. Pat. No. 4,565,807. A solution of cyclodextrin and modafinil has been reported in Rambert, F. A., et al. *Neuropsychopharmacology,* 1994, 10(3S), Part 2, 169S. It was reported that 1% and 2% aqueous hydroxypropyl-β-cyclodextrin solutions were prepared for intracerebroventricular injection in rats. However, these solutions were relatively dilute, contain a low concentration of modafinil, and were administered by direct injection into the brain, and not by oral means.

While cyclodextrins have pharmaceutical applications and have been used to solubilize or stabilize many compounds, these uses have had more limited applicability to therapeutic agents and there are many compounds for which cyclodextrin complexation is either not possible, or present disadvantages which render them unsuitable for pharmaceutical use. See J. Szejtli, *Pharmaceutical Technology,* 1991, 24–38; and U.S. Pat. No. 5,362,860. In particular, the bioavailability of a drug:cyclodextrin mixture is often unpredictable, and indeed formation of drug:cyclodextrin complexes often result in decreased drug bioavailability. See T. Loftsson, *Pharmaceutical Technology,* 1999, 12, 40–50; and Uekama, K, et al., *CRC Critical Reviews in therapeutic Drug Carrier Systems,* 1987, 3(1), 1–40.

It has been found by the present inventors that modafinil compound:cyclodextrin mixtures provide for bioavailable delivery of a modafinil compound. While cyclodextrins can increase solubilization of a drug, there is not necessarily a direct correlation to an increase in bioavailability of the drug, or in particular, to bioavailability through oral administration. The mechanisms for drug absorption in these systems are more complicated than a simple correlation to the solubilization profile, as evidenced by the fact that formation of drug-β-cyclodextrin complexes often result in decreased drug bioavailability. The complex itself cannot penetrate a membrane barrier, thus the drug must dissociate from the complex prior to crossing a barrier. The dissociation of the drug is reflected in the stability constant of the drug:complex equilibrium. A stability constant that generally leads to complex formation may also lead to overlability and premature drug release, while very stable complexes can result in retarded or incomplete release of the drug. Furthermore, a high cyclodextrin concentration or the presence of excipients may additionally hinder complex dissociation, and therefore the absorption of the drug.

The present invention provides for complexes of a modafinil compound and a cyclodextrin particularly inclusion complexes, which provide for enhanced aqueous solubility of the modafinil compound at pharmaceutically useful concentrations, and offer enhanced pharmacological properties. It has been found that such complexes can provide bioavailability of the modafinil compound, in particular, oral bioavailability, as well as effectively taste-mask the modafinil compound thereby providing palatable liquid compositions.

SUMMARY OF THE INVENTION

One object of the present invention is to provide complexes of a modafinil compound and a cyclodextrin. Preferably the modafinil compound in the presence of a cyclodextrin has an aqueous solubility of at least 10 mg/ml. Preferably the modafinil compound is modafinil, the cyclodextrin is a β-cyclodextrin and the complex is an inclusion complex. In certain embodiments, the complex can be a solid, or the complex can be in solution.

Another object is to provide complexes of a modafinil compound and a cyclodextrin, wherein the modafinil compound is bioavailable upon oral administration to a subject.

An additional object of the invention is to provide compositions of a modafinil compound and a cyclodextrin. Preferably the modafinil compound in the presence of a cyclodextrin has an aqueous solubility of at least 10 mg/ml. In preferred embodiments, the compositions are pharmaceutically acceptable, and may further comprise one or more pharmaceutically acceptable excipients. In other preferred embodiments, the modafinil compound is modafinil, the cyclodextrin is a β-cyclodextrin, and the compositions comprise a complex, preferably an inclusion complex of modafinil and a cyclodextrin. In another preferred embodiment, the composition is aqueous and suitable for oral consumption.

Another object of the invention is to provide a method of preparing a complex of a modafinil compound and a cyclodextrin by contacting the modafinil compound with the cyclodextrin. In certain embodiments, the complex is prepared in an aqueous medium. In certain preferred embodiments, the complex comprises an inclusion complex of modafinil and a β-cyclodextrin. In other embodiments, the complex is dried and isolated as a solid.

A further object of the present invention is to provide a method for treating a disease or disorder by administering to a subject in need thereof a therapeutically effective amount of a composition of a modafinil compound and a cyclodextrin. Preferably, the composition comprises an inclusion complex of modafinil and a cyclodextrin, and is suitable for oral administration.

An additional object of the invention is to provide a composition of a modafinil compound and a cyclodextrin which provides at least a 10% increase in the blood serum level in mammals relative to a solid dose of a modafinil compound without cyclodextrin. In certain preferred embodiments, the composition is a solution, and more preferably, is an aqueous solution. In other preferred embodiments, the modafinil compound is modafinil, and the subject is mammal, preferably a rat or a human.

Another object of the present invention is to provide a composition of a modafinil compound and a cyclodextrin which provides at least a 25% increase in the blood serum level in mammals in the first hour of administration relative to a solid dose of a modafinil compound without a cyclodextrin. In certain preferred embodiments, the composition is a solution, and more preferably, is an aqueous solution. In other preferred embodiments, the modafinil compound is modafinil, and the mammal is a rat or a human.

Still another object of the invention is to provide a composition of a modafinil compound and a cyclodextrin, wherein the modafinil compound is taste-masked. In certain preferred embodiments, the composition is palatable and is suitable for oral administration in a mammal, preferably a human.

Yet another object is to provide a composition of a modafinil compound and a cyclodextrin which upon oral administration provides substantially the blood serum profile of FIG. 1, in a mammal, preferably a rat or human.

DETAILED DESCRIPTION OF THE INVENTION

Figure 1:
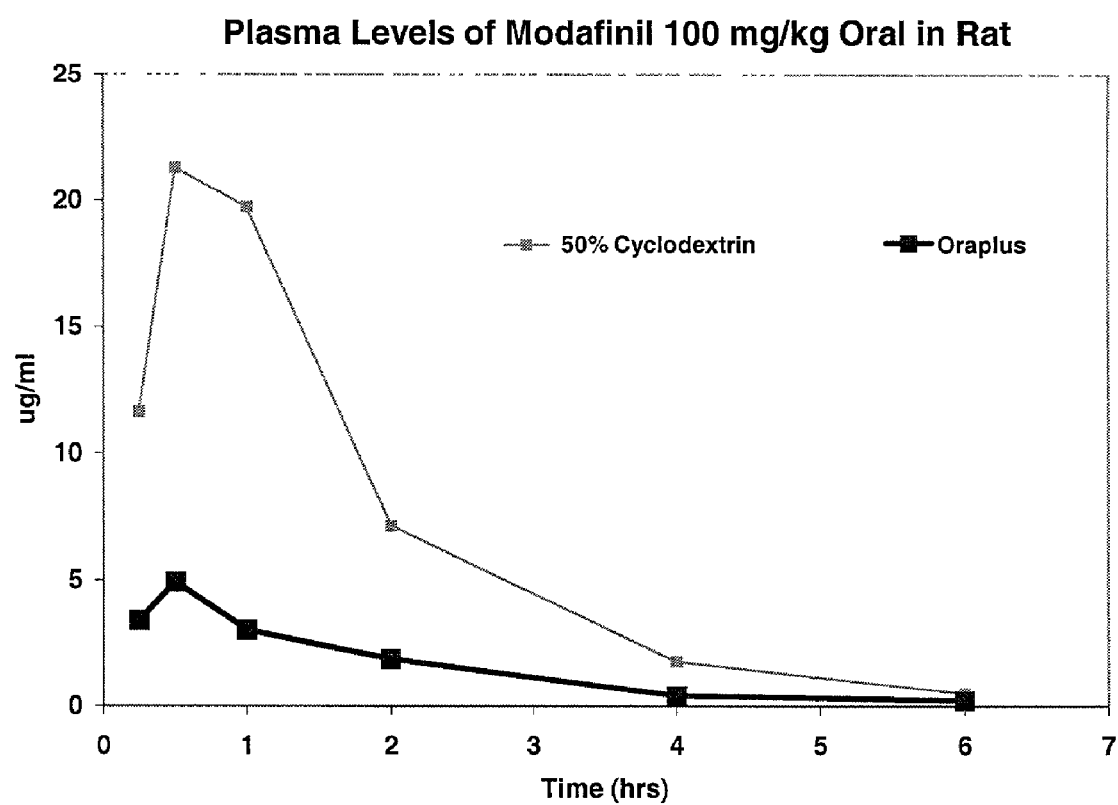
FIG. 1 shows the blood serum profiles of a 50% cyclodextrin:modafinil solution and an Oraplus® suspension of modafinil upon oral administration in rats, as shown in Example 3.

The present invention provides for mixtures of a modafinil compound with a cyclodextrin, and preferably the modafinil compound in the presence of a cyclodextrin has an aqueous solubility of at least 10 mg/ml. One aspect of the invention involves a modafinil compound:cyclodextrin complex, and another aspect involves pharmaceutical compositions of the modafinil compound:cyclodextrin complex. Preferably the complex is an inclusion complex.

As used herein, a "complex" refers to an association of molecules formed by non-covalent interactions between the molecules. This is typically an equilibrium process in solution, and can also exist in the solid state. In a preferred embodiment, the complex is an inclusion complex.

As used herein, an "inclusion complex" refers to any structure where a guest molecule is either partially or completely contained within the cavity of a host macrocyclic molecule. In the present invention, the guest molecule is a modafinil compound, preferably modafinil, and the host macrocyclic molecule is a cyclodextrin.

As used herein, "a modafinil compound" or "modafinil compound" and the like, refers to modafinil, its racemic mixtures, individual isomers, acid addition salts, such as a metabolic acid of modafinil, benzhydrylsulfinylacetic acids, and its sulfone forms, hydroxylated forms, polymorphic forms, analogs, derivatives, cogeners and prodrugs thereof. Prodrugs are known in the art as compounds that are converted to the active agent (a modafinil compound) in the body of a subject. In preferred embodiments, the modafinil compound is modafinil.

As used herein, "a cyclodextrin" refers to the natural cyclodextrins, α-cyclodextrin, β-cyclodextrin, and γ-cyclodextrin, and their respective derivatives. Preferably, the cyclodextrin is a β-cyclodextrin, which includes β-cyclodextrin and its derivatives. More preferably, the cyclodextrin is β-cyclodextrin, hydroxypropyl-β-cyclodextrin and β-cyclodextrin sulfobutyl ether.

As used herein, "modafinil compound:cyclodextrin mixtures" refers to a combination of a modafinil compound and a cyclodextrin. In particular, the mixtures refer to either a complex of a modafinil compound and a cyclodextrin, or a composition comprising a modafinil compound and a cyclodextrin. In certain embodiments, the mixtures comprise a modafinil compound:cyclodextrin complex as either a solid, or in solution.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "therapeutically effective amount" refers to an amount which is effective in reducing, eliminating, treating, preventing or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, "bioavailable" refers to a portion of the administered dose that is absorbed in the blood stream and can readily be determined by techniques known in the art, such as, for example, by measuring the blood serum level of a compound, and in particular by calculating the area under the curve in a blood serum profile.

As used herein, the term "subject" refers to a warm blooded animal such as a mammal, preferably a human or a human child, which is afflicted with, or has the potential to be afflicted with one or more diseases and conditions described herein.

As used herein, "unit dose" means a single dose which is capable of being administered to a patient, and which can be readily handled and packaged, remaining as a physically and chemically stable unit dose, comprising either a modafinil compound or a pharmaceutically acceptable composition comprising a modafinil compound.

As used herein, "excipients" refers to substances that are used in the formulation of pharmaceutical compositions, and, by themselves, generally have little or no therapeutic value. Typical excipients include antioxidants, anti-bacterial agents and other preservatives; chelating agents; buffering agents; agents for adjusting toxicity; coloring, flavoring and diluting agents; emulsifying and suspending agents; and other substances commonly used in pharmaceutical applications.

As used herein, the term "about" refers to a range of values ±10% of a specified value. For example, the phrase "about 20" includes ±10% of 20, or from 18 to 22.

In a first embodiment, the present invention provides a complex of a modafinil compound and a cyclodextrin, and preferably a complex of modafinil and a β-cyclodextrin. In a more preferred embodiment, the complex is an inclusion complex. The complex or inclusion complex may be a solid or in solution. The solid complex may be administered directly to a subject, or may be reconstituted in an aqueous environment. The solid complex can be contacted with an aqueous medium in vitro, that is subject to predilution prior to administration to the subject, or in vivo, that is, contacted with aqueous environment of the subject, such as in the gastrointestinal tract. The complex can also be present in a liquid solution, preferably an aqueous solution, and may be administered directly to a subject.

In another embodiment, the present invention provides for compositions comprising a modafinil compound and a cyclodextrin. Preferably the composition is pharmaceutically acceptable, and optionally further comprises one or more pharmaceutically acceptable excipients. In another embodiment, the compositions comprise a complex of a modafinil compound and a cyclodextrin. Preferably, the complex is an inclusion complex. Furthermore, the composition may be a solid or a solution, preferably an aqueous solution.

Any cyclodextrin which enhances the aqueous solubility and/or provides for bioavailable delivery of a modafinil compound may be used in the present invention. A preferred cyclodextrin is one which yields a complex with the modafinil compound, and more preferably, yields an inclusion complex. Preferably the cyclodextrin allows for bioavailability of the modafinil compound, and more preferably allows for bioavailability equal to or greater than that of the solid tablet form. In another aspect, the appropriate cyclodextrin taste-masks the modafinil compound.

The cyclodextrins of the present invention can include the natural occurring cyclodextrins and their derivatives. The natural cyclodextrins include α-cyclodextrin, β-cyclodextrin, and γ-cyclodextrin, with a preferred being β-cyclodextrin. Derivatives are typically prepared by modifying the hydroxyl groups located on the exterior, or hydrophilic side of the cyclodextrin. The modifications can be made to increase the aqueous solubility and the stability of the complex and can modify the physical characteristics of the complex including the formation and dissociation of the complex. The types and degree of modification, as well as their preparation, are well known in the art. See, for example, Szejtli, J., *Cyclodextrins and Their Inclusion Complexes,* Akadémiai Kiadó: Budapest, 1982; U.S. Pat. No. 5,024,998; U.S. Pat. No. 5,874,418 and U.S. Pat. No. 5,660,845, and references contained therein, all of which are incorporated herein in their entireties.

Any of the natural cyclodextrins can be derivatized, with derivatives of β-cyclodextrin being preferred. Cyclodextrin derivatives include alkylated cyclodextrins, preferably methyl-, dimethyl-, trimethyl- and ethyl-β-cyclodextrins; hydroxyalkylated cyclodextrins, including hydroxyethyl-, hydroxypropyl-, and dihydroxypropyl-β-cyclodextrin; ethylcarboxymethyl cyclodextrins; sulfate, sulfonate and sulfoalkyl cyclodextrins, preferably β-cyclodextrin sulfate, β-cyclodextrin sulfonate, and β-cyclodextrin sulfobutyl ether; as well as polymeric cyclodextrins. Other cyclodextrin derivatives can be made by substitution of the hydroxy groups with saccharides, such as glucosyl- and maltosyl-β-cyclodextrin.

Preferred cyclodextrins include the naturally occurring cyclodextrins, methyl-β-cyclodextrin, dimethyl-β-cyclodextrin, trimethyl-β-cyclodextrin, 2-hydroxymethyl-β-cyclodextrin, hydroxyethyl-β-cyclodextrin, 2-hydroxypropyl-β-cyclodextrin, 3-hydroxypropyl-β-cyclodextrin, β-cyclodextrin sulfate, β-cyclodextrin sulfonate, or β-cyclodextrin sulfobutyl ether. Most of these are commercially available from such suppliers as Aldrich Chemical Company, Milwaukee Wis. and Wacker Chemicals, New Canaan, Conn. More preferred cyclodextrins include β-cyclodextrin, hydroxypropyl-β-cyclodextrin and β-cyclodextrin sulfobutyl ether.

A preferred cyclodextrin is one which improves the aqueous solubility of the modafinil compound of 0.44 mg/ml, and more preferably allows for a pharmaceutically useful concentration of a modafinil compound. Preferably the aqueous solubilization of the modafinil compound is at least about 10 mg/ml, and more preferably is at least 20 mg/ml. In certain embodiments, the solubility of a modafinil compound is from about 10 or 20 to about 100 mg/ml, more preferably from about 10 to about 50 mg/ml. In other embodiments, the solubility of a modafinil compound is from about 20 to about 50 mg/ml.

The aqueous solubility of the modafinil compound can be enhanced by the formation of a complex, preferably an inclusion complex, with a cyclodextrin. The degree of complexation can vary, and is dependant on the size of the drug, the degree of inclusion, the type of cyclodextrin and the concentration of the cyclodextrin. The molar ratio of drug:cyclodextrin inclusion complexes can vary. The present inventors have found that modafinil:cyclodextrin has a molar ratio of 1:1, that is, one molecule of the drug fits within the cavity of one cyclodextrin molecule. The present invention contemplates a molar ratio of cyclodextrin to a modafinil compound to be in the range from about 0.8:1 to 10:1, preferably from about 1:1 to about 3:1, and most preferably about 1:1. The molar ratio can be readily determined by preparing a saturated cyclodextrin solution, and mixing the drug to form the complex. The complex can then be isolated by the various means described herein, and the complex can be analyzed to determine the proper ratio.

Various methods are known in the art to prepare drug:cyclodextrin complexes, including the solution method, co-precipitation method, the slurry method, the kneading method and the grinding method. See T. Loftsson, *Pharmaceutical Technology*, 1999, 12, 41–50. In the solution method, the drug, either as a solid or in a solution, is added to a solution containing an excess amount of cyclodextrin. It is also possible to add an excess of the drug to an aqueous cyclodextrin solution. The mixture is agitated, and may optionally be heated, until an equilibrium is reached, which may take several hours or several days. The equilibrated solution is then filtered or centrifuged to give a clear solution of the drug-cyclodextrin complex. The clear solution can be directly administered to a subject, or a solid complex can be obtained by removal of the water by evaporation (such as spray-drying), sublimation (such as lyophilization) or other drying means well known in the art.

A solid complex may also be obtained by the precipitation method. Often, the cyclodextrin complexes precipitate upon cooling of the solution. Otherwise, a solvent in which the complex has minimal solubility, typically an organic solvent, is used to precipitate the solid complex. The precipitate containing the complex can then be filtered or centrifuged to obtain a solid drug-cyclodextrin complex. A generally less effective method of preparing a solid complex mixture is to grind a dry mixture of the drug and cyclodextrin in a sealed container which is then gently heated to a temperature between 60–140° C.

If the drug is poorly water-soluble, the slurry or kneading methods can be employed. The drug and cyclodextrin can be suspended in water to form a slurry, which is similarly stirred and/or heated to equilibration. The complex can be collected by filtration or by evaporation of the water. The kneading method is similar to the slurry method, whereby the drug and cyclodextrin are mixed with a minimal amount of water to form a paste. The complex can be isolated by methods similar to those discussed above.

There are various physicochemical methods to determine the formation of an inclusion complex in solution, including UV, circular dichroism and fluorescence spectroscopy. Nuclear magnetic resonance and potentiometry can also show complexation. Solid cyclodextrin complexes can be studied by powder X-ray diffractometry, differential scanning calorimetry or thermogravimetry.

The above methods generally utilize an excess amount of cyclodextrin to maximize equilibration of a cyclodextrin:drug complex. The amount of cyclodextrin in the desired formulation is directly related to the amount of the desired drug concentration and the molar ratio of cyclodextrin:drug in the complex. The present inventors have found that modafinil typically forms a 1:1 complex with β-cyclodextrin. As such, a 2% hydroxypropyl-β-cyclodextrin ("HPβCD") solution will then solubilize about 4.4 mg/ml of a modafinil compound. A 20% HPβCD solution will solubilize about 39.5 mg/ml of modafinil. A 40% HPβCD solution solubilizes about 78.4 mg/ml of modafinil. The typical saturation point of HPβCD in water is about 50%. Solutions with greater than about 30% HPβCD can form a 1:1 inclusion complex with an equivalent amount of modafinil, but generally get cloudy upon cooling to room temperature. Hence, less than 1 molar equivalent of modafinil is typically used at these higher concentrations of cyclodextrin.

The modafinil compound:cyclodextrin mixtures of the present invention comprise modafinil compounds, which may be readily prepared by one skilled in the art using conventional methods. Methods for preparing modafinil and various derivatives appear in U.S. Pat. No. 4,177,290, and methods for preparing other modafinil compounds appear in U.S. Pat. Nos. 4,927,855, 5,719,168 and in U.S. patent application Ser. No. 60/204,789.

A therapeutically effective amount of the modafinil compound:cyclodextrin mixtures can be administered for the treatment of a disease or disorder. In particular, the mixtures can be used in the treatment of sleepiness, such as excessive daytime sleepiness associated with narcolepsy, or sleepiness associated with sleep apneas, tiredness, Parkinson's disease, cerebral ischemia, stroke, sleep apneas, eating disorders, attention deficit hyperactivity disorder, cognitive dysfunction or fatigue, such as fatigue resulting from multiple sclerosis ("MS fatigue"); and for promotion of wakefulness, stimulation of appetite, or stimulation of weight gain.

In certain embodiments, the modafinil compound:cyclodextrin mixtures comprise at least one unit dose of a modafinil compound. In certain more preferred embodiments, the mixtures comprise one unit dose of modafinil. Preferable daily doses of modafinil range from about 0.01 to 100 mg/kg of body weight. By way of general guidance, daily doses for humans range from about 0.1 mg to about 2000 mg. Preferably the unit dose range is from about 1 to about 500 mg administered one to four times a day, and even more preferably from about 10 mg to about 400 mg, one to two times a day. In certain preferred embodiments, the unit dose is 100 or 200 mg. In other preferred embodiments, a unit dose is one that is necessary to achieve a blood serum level of about 0.05 to 30 μg/ml, and more preferably, of about 1 to about 20 μg/ml in a subject.

In other embodiments, the addition of a cyclodextrin can enhance the bioavailability of a modafinil compound. Preferably, the modafinil compound is bioavailable upon oral administration. The bioavailability of a modafinil compound can be measured by tracing the blood serum level of the modafinil compound in a subject over time. The solid tablet form of a modafinil compound is used as a basis for comparison. In a certain embodiment, the modafinil compound:cyclodextrin mixtures provide substantially the blood serum level profile shown in FIG. 1 when administered to a subject. Any blood serum level profile is substantially that of FIG. 1 if the profile falls within ±15% of either the 50% cyclodextrin:modafinil curve in FIG. 1, or the blood serum concentrations of modafinil at 0.25, 0.5, 1, 2, 4 and 6 h as shown in Table 2. Preferably the blood serum level profile is obtained upon administration to humans or rats.

In other embodiments, the modafinil compound:cyclodextrin mixtures provide at least a 25% increase in the blood serum level relative to a solid dose of a modafinil compound. In particular, the modafinil compound:cyclodextrin mixtures provide from about a 25–500% increase, preferably from about a 25–200% increase, and more preferably a 25–100% increase in blood serum levels over time. In certain embodiments, the blood serum level profile was obtained upon administration to humans or rats. Preferably the modafinil compound: cyclodextrin complex is in solution.

In addition, the modafinil compound:cyclodextrin mixtures can provide a sharp increase of the modafinil compound in the blood serum within the first hour of administration. In certain embodiments, the modafinil compound:cyclodextrin mixtures provides at least about a 50% increase in the blood serum level within the first hour of administration, relative to the solid dose of modafinil. In particular, the increase ranges from about 50–400%, preferably from about 50–200% increase, and more preferably a 50–100% increase in blood serum levels within the first hour of administration relative to a solid dose of modafinil. In certain embodiments, the blood serum level profile is obtained upon administration to humans or rats. Preferably the modafinil compound:cyclodextrin complex is in solution.

In a further embodiment, cyclodextrins mask the bitter taste of the modafinil compound, thereby making the modafinil compound more palatable. The modafinil compounds, in granular form, or in solution have a bitter, metallic taste, making them less desirable for oral administration. The compositions of the present invention comprise a modafinil compound and a cyclodextrin wherein the modafinil compound is effectively taste-masked. Preferably, the modafinil compound is complexed with the cyclodextrin. In certain embodiments, the taste-masked composition is a solution, preferably an aqueous solution. In other embodiments, the taste-masked composition is a solid. In certain preferred embodiments, the modafinil compound in the presence of a cyclodextrin has a concentration of at least 10 mg/ml, and more preferably has a concentration of at least 20 mg/ml In yet another embodiment, the present invention provides for modafinil compound:cyclodextrin mixtures that are suitable for oral or parenteral administration to a subject. A preferred mode of administration is oral, and includes ingestion in the form of a liquid composition, such as a solution, syrup, or elixir; or as a solid, such as a tablet, capsule or powder or granular form for direct administration or for re-constitution in an aqueous solution.

In certain embodiments, the mixtures are contained in a capsule. In particular, aqueous mixtures are generally contained in hard capsules, comprising gelatin, hydroxypropylmethylcellulose ("cellulose"), or starch, while in general, solid or predominantly non-aqueous mixtures are generally contained in soft gelatin capsules. In other embodiments, the mixtures are in a syrup or elixir. Syrups typically comprise 85% sucrose in water, and elixirs typically comprise about 25% alcohol. The syrups and elixirs optionally further comprise sweetening and flavoring agents, as well as other excipients known in the art.

The compositions may also be prepared in admixture with additional pharmaceutically-acceptable excipients to further promote effective therapeutic use. The excipients may include lipids, for example, those which are useful to change particle size; antibacterial agents such as benzyl alcohol or methyl paraben; antioxidants such as ascorbic acid, sodium bisulfite, and fatty acid esters of ascorbic acid, such as ascorbyl palmitate; chelating agents such as ethylene diaminetetraacetic acid; buffers such as acetates, citrates or phosphates and agents for the adjustment of tonicity such as sodium chloride or dextrose; binders, such as various starches and celluloses, agar, gum arabic, and traganth gum; lubricants, such as talc, magnesium or calcium stearate or aluminum silicate; or other excipients such as flavorings, sweetening agents and coloring agents. Other appropriate excipients, appropriate to their form, can readily be determined by one skilled in the art, and may further include those found in *The Handbook of Pharmaceutical Excipients*, 2nd Ed.; The Pharmaceutical Press: London, 1994.

The materials, methods, and examples presented herein are intended to be illustrative, and not to be construed as limiting the scope or content of the invention. Unless otherwise defined, all technical and scientific terms are intended to have their art-recognized meanings.

EXAMPLES

A. Materials:

All the materials in the following examples are commercially available or can be readily prepared by one skilled in the art by known or readily available literature methods. Hydroxypropyl-β-cyclodextrin was purchased as C* Cavitron 82005, from Cerestar USA, Inc., Hammond, Ind. A taste-masking agent, Bell Bitter Blocker was purchased from Bell Flavors and Fragrances, Northbrook, Ill. A sweetener, Pharmasweet powder was purchased from Crompton and Knowles, Mahwah, N.J. The solvents were USP/NF grade or better.

B. Methods:

1 HPLC Measurement of Modafinil Concentrations

The following HPLC method may be used to measure the modafinil compound content in the compositions. Filter a solution saturated with a modafinil compound through a 1.2 μm syringe filter. Dilute 10μL of the clear solution to 1 mL with 990μL of dimethylsulfoxide (Fischer Certified ACS grade). Take 10 μL of the diluted solution for the HPLC analysis, with the following representative column conditions:

Flow rate: 1.2mL/min.
Column: ODS, 4.6×20mm, Column Temp: 30° C.
Mobil phase: 80%(65% Acetonitrile/35%1M phosphate buffer) 20% water
Analysis time: 5 minutes
Wavelength: 222 nanometers Concentration can be calculated by comparison to area from a modafinil compound standard used at 0.4mg/mL with appropriate dilution.

2. Method for Measurements of Blood Level in Rats Given Modafinil Solutions

Adult male Sprague-Dawley rats were allowed to fast overnight prior to administration. Each formulation was administered to the rats via oral gavage, with the dose of a modafinil compound being 100 mg/kg in a dose volume of 3.3 ml/kg. Blood was collected from the lateral tail vein at 0.25, 0.5, 1, 2, 4 and 6 hours post dose. The blood was put on wet ice and centrifuged at 13,000 RPM for 10 minutes. The supernatant (plasma) was collected and frozen on dry ice, and stored at −70° C. until analysis. The blood serum levels of the modafinil compound in these experiments were measured by LC/MS.

Example 1

Preparation of Modafinil in Aqueous 50% Hydroxypropyl-β-Cyclodextrin Solution

A solution of hydroxypropyl-β-cyclodextrin (3.53 grams) in 3.54 grams of water was stirred with warming at 60–70° C. to give a clear, slightly viscous solution. To this solution modafinil(micronized)(0.1815 grams) was added in one portion and stirred until no particulate matter remained. Cooling to room temperature gave a volume of near 6 mL with no precipitate formation and a modafinil concentration of approximately 30 mg/mL.

Example 2

Syrup Formulations of Modafinil:HPβCD Mixtures

The following formulations were prepared by combining the ingredients listed below and warming the solution to 65–70° C. The formulations are clear upon cooling to room temperature.

TABLE 1

Exemplary Modafinil: HPβCD Syrup Formulations

| EXAMPLE | INGREDIENTS | AMOUNT/GRAMS |
| --- | --- | --- |
| 2-A | 1) Modafinil | 0.38 |
|  | 2) 70% maltitol | 8.38 |
|  | 3) 40% (w:w) aq. C* Cavitron 82005 | 35.32 |
| 2-B | 1) Modafinil | 0.11 |
|  | 2) 85% maltitol | 2.72 |
|  | 3) 50% (w:w) aq. C* Cavitron 82005 | 9.39 |
|  | 4) Bell Bitter Blocker | 0.36 |
|  | 5) Pharmasweet powder | 0.01 |
| 2-C | 1) Modafinil | 0.10 |
|  | 2) 50% (w:w) aq. C* Cavitron 82005 | 7.97 |
|  | 3) Sucrose | 2.36 |
|  | 4) 67% (w:w) aq. Sucrose syrup | 2.12 |
|  | 5) Sodium saccharin | 0.08 |
|  | 6) Pharmasweet powder | 0.01 |
| 2-D | 1) Modafinil | 0.10 |
|  | 2) 50% (w:w) aq. C* Cavitron 82005 | 8.53 |
|  | 3) 67% (w:w) aq. Sucrose syrup | 0.40 |
|  | 4) Corn Syrup | 2.77 |
|  | 5) Pharmasweet powder | 0.01 |

Example 3

Blood Serum Levels of Modafinil in Rats

The blood serum levels of modafinil in rats, upon administration of compositions of Example 1, is shown below in Table 2. The Oraplus® composition is intended to mimic the bioavailability of solid modafinil dosed in an oral fashion such as a tablet, but without the difficulty of administering a tablet to the rat. Oraplus® is an oral suspending vehicle that is commercially available (Paddock Laboratories, Minneapolis, Minn. ), and is primarily composed of purified water, microcrystalline cellulose, sodium carboxymethylcellulose, xanthan gum, carrageenan, citric acid and sodium phosphate (as buffers), simethicone (antifoaming agent), and potassium sorbate and methyl paraben (preservatives).

TABLE 2

Blood Serum Levels of Modafinil in Rats

| Modafinil Solutions TIME (Hrs.) | Example 1 | Oraplus |
| --- | --- | --- |
| 0.25 | 11.65 | 3.4 |
| 0.5 | 21.3 | 4.9 |
| 1 | 19.7 | 3.0 |
| 2 | 7.1 | 1.9 |
| 4 | 1.8 | 0.4 |
| 6 | 0.5 | 0.2 |

This data is represented graphically in FIG. 1.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A method of treating at least one disease or disorder selected from the group consisting of sleepiness, tiredness, Parkinson's disease, cerebral ischemia, stroke, sleep apneas, eating disorders, attention deficit hyperactivity disorder, cognitive dysfunction, fatigue, lack of wakefulness, lack of appetite, and lack of weight gain, comprising the step of orally administering to a mammal a therapeutically effective amount of a modafinil compound:cyclodextrin mixture, wherein the mixture provides an aqueous solubility of the modafinil compound of at least about 30 mg/mL, and wherein the cyclodextrin is selected from the group consisting of a hydroxypropyl-β-cyclodextrin, β-cyclodextrin sulfobutyl ether, and mixtures thereof.

2. The method of claim 1, wherein the modafinil compound:cyclodextrin mixture comprises an inclusion complex of the modafinil compound and the cyclodextrin.

3. The method of claim 1, wherein the modafinil compound is modafinil.

4. The method of claim 3, wherein the modafinil compound is the levorotatory form of modafinil.

5. The method of claim 1, wherein the cyclodextrin is β-cyclodextrin sulfobutyl ether.

6. The method of claim 5, wherein the modafinil compound is modafinil.

7. The method of claim 6, wherein the modafinil compound is the levorotatory form of modafinil.

8. The method of claim 1, wherein the cyclodextrin is 2-hydroxypropyl-β-cyclodextrin.

9. The method of claim 8, wherein the modafinil compound is modafinil.

10. The method of claim 9, wherein the modafinil compound is the levorotatory form of modafinil.

11. The method of claim 1, wherein the modafinil compound:cyclodextrin mixture is in a solution form.

12. The method of claim 1, wherein the modafinil compound:cyclodextrin mixture is in a solid form.

13. The method of claim 1, wherein the modafinil compound:cyclodextrin mixture contains the cyclodextrin and the modafinil compound at a molar ratio of about 0.8:1 to 10:1.

14. The method of claim 1, wherein the modafinil compound:cyclodextrin mixture contains the cyclodextrin and the modafinil compound at a molar ratio of about 1:1 to about 3:1.

15. The method of claim 1, wherein the modafinil compound:cyclodextrin mixture contains the cyclodextrin and the modafinil compound at a molar ratio of about 1:1.

16. The method of claim 1, wherein the modafinil compound is modafinil, the cyclodextrin is 2-hydroxypropyl-β-cyclodextrin, and the modafinil compound:cyclodextrin mixture contains 2-hydroxypropyl-β-cyclodextrin and modafinil at a molar ratio of about 1:1.

17. The method of claim 16, wherein the modafinil compound is the levorotatory form of modafinil.

18. The method of claim 1, wherein the modafinil compound:cyclodextrin mixture is orally administered to treat sleepiness, to promote wakefulness, to stimulate appetite, or to stimulate weight gain.

19. The method of claim 1, wherein the modafinil compound:cyclodextrin mixture comprises at least one unit dose of the modafinil compound.

20. The method of claim 19, wherein the unit dose is form about 10 mg to about 400 mg.

21. The method of claim 19, wherein the unit dose is 100 mg or 200 mg.

22. The method of claim 1, wherein oral administration of the modafinil compound:cyclodextrin mixture provides at least a 10% increase in the blood serum level of the modafinil compound relative to the same amount of the modafinil compound in a solid oral dosage form.

23. The method of claim 1, wherein oral administration of the modafinil compound:cyclodextrin mixture provides at least a 25% increase in the blood serum level of the modafinil compound relative to the same amount of the modafinil compound in a solid oral dosage form.

24. The method of claim 1, wherein oral administration of the modafinil compound:cyclodextrin mixture provides at least a 50% increase in the blood serum level of the modafinil compound relative to the same amount of the modafinil compound in a solid oral dosage form.

25. The method of claims 22, 23, or 24 wherein the increase in the blood serum level is within the first hour of oral administration to the mammal.

26. The meted of claim 1, wherein oral administration of the modafinil compound:cyclodextrin mixture provides substantially the blood serum profile of FIG. 1.

27. A method of delivering a modafinil compound to the bloodstream of a mammal comprising the step of orally administering to the mammal a modafinil compound:cyclodextrin mixture, wherein the mixture provides an aqueous solubility of the modafinil compound of at least about 30 mg/mL, and wherein the cyclodextrin is selected from the group consisting of a hydroxypropyl-β-cyclodextrin, β-cyclodextrin sulfobutyl ether, and mixtures thereof.

28. The method of claim 27, wherein the modafinil compound is modafinil.

29. The method of claim 28, wherein the modafinil compound is the levorotatory form of modafinil.

30. The method of claim 27, wherein the cyclodextrin is a hydroxypropyl-β-cyclodextrin.

31. The method of claim 27, wherein the modafinil compound:cyclodextrin mixture contains the cyclodextrin and the modafinil compound at a molar ratio of about 1:1.

32. The method of claim 27, wherein the modafinil compound:cyclodextrin mixture comprises at least one unit dose of the modafinil compound.

33. The method of claim 32, wherein the unit dose is 100 mg or 200 mg.

34. The method of claim 27, wherein oral administration of the modafinil compound:cyclodextrin mixture provides at least a 10% increase in the blood serum level of the modafinil compound relative to the same amount of the modafinil compound in a solid oral dosage form.

35. The method of claim 1, wherein the cyclodextrin masks the taste of the modafinil compound.

36. The method of claim 27, wherein the cyclodextrin masks the taste of the modafinil compound.

* * * * *